(12) United States Patent
Beaupre

(10) Patent No.: US 6,436,115 B1
(45) Date of Patent: *Aug. 20, 2002

(54) BALANCED ULTRASONIC BLADE INCLUDING A PLURALITY OF BALANCE ASYMMETRIES

(76) Inventor: Jean M. Beaupre, 9200B Hunters Creek, Cincinnati, OH (US) 45242

( * ) Notice: Subject to any disclaimer, the term of this patent is extended or adjusted under 35 U.S.C. 154(b) by 0 days.

This patent is subject to a terminal disclaimer.

(21) Appl. No.: 09/660,024

(22) Filed: Sep. 12, 2000

Related U.S. Application Data

(63) Continuation of application No. 09/499,989, filed on Feb. 8, 2000, now Pat. No. 6,328,751, which is a continuation of application No. 09/106,686, filed on Jun. 29, 1998, now abandoned.

(51) Int. Cl.[7] .............................................. A61B 17/32
(52) U.S. Cl. ..................................................... 606/169
(58) Field of Search ............................... 606/169, 167; 604/22

(56) References Cited

U.S. PATENT DOCUMENTS 2,990,616 A  7/1961  Balamuth et al. ............... 32/26
3,053,124 A  9/1962  Balamuth et al. ............... 78/82

(List continued on next page.)

FOREIGN PATENT DOCUMENTS

EP  203 229        12/1983
EP  0 830 845 A1   9/1996

OTHER PUBLICATIONS

International Standard IEC 61847, First edition 1998–01, Ultrasonics—Surgical systems—Measurement and declaration of the basic output characteristics ©IEC 1998.

*Primary Examiner*—Michael H. Thaler

(57) ABSTRACT

A balanced ultrasonic surgical instrument is described wherein the balanced ultrasonic surgical instrument includes an ultrasonic transmission rod and an ultrasonically actuated blade attached to the distal end of the ultrasonic transmission rod. According to the present invention, the ultrasonically actuated blade includes a treatment portion and a balance portion. The treatment portion has a functional feature such as, for example, a curved blade which makes the treatment portion asymmetric. The balance portion includes at least first and second asymmetric balance features designed and positioned to balance out any undesirable torque generated by the treatment portion. The balance portion further extends generally from a node point on the ultrasonic transmission rod to the proximal end of the treatment portion.

24 Claims, 8 Drawing Sheets

U.S. PATENT DOCUMENTS

| | | | |
|---|---|---|---|
| 3,526,219 A | 9/1970 | Balamuth | 128/2 |
| 3,830,240 A | 8/1974 | Antonevich et al. | 128/328 |
| 3,861,391 A | 1/1975 | Antonevich et al. | 128/328 |
| 3,990,452 A | 11/1976 | Murry et al. | 128/305 |
| 4,136,700 A | 1/1979 | Broadwin et al. | 128/305 |
| 4,169,984 A | 10/1979 | Parisi | 310/323 |
| 4,526,571 A | 7/1985 | Wukchinich | 604/22 |
| 4,634,419 A | 1/1987 | Kreizman et al. | 604/22 |
| 4,911,161 A | 3/1990 | Schechter | 606/171 |
| 4,920,954 A | 5/1990 | Alliger et al. | 128/24 |
| 4,974,581 A | 12/1990 | Wiksell | 128/24 A |
| 4,992,048 A | 2/1991 | Goof | 433/102 |
| 5,019,083 A | 5/1991 | Klapper et al. | 606/99 |
| 5,047,008 A | 9/1991 | de Juan, Jr. et al. | 604/22 |
| 5,047,043 A | 9/1991 | Kubota et al. | 606/169 |
| 5,180,363 A | 1/1993 | Idemoto et al. | 202/32 |
| 5,188,102 A | 2/1993 | Idemoto et al. | 128/24 AA |
| 5,205,817 A | 4/1993 | Idemoto et al. | 604/22 |
| 5,221,282 A | 6/1993 | Wuchinich | 606/99 |
| 5,222,937 A | 6/1993 | Kagawa | 604/22 |
| 5,248,296 A | 9/1993 | Alliger | 609/22 |
| 5,312,329 A | 5/1994 | Beaty et al. | 604/22 |
| 5,318,570 A | 6/1994 | Hood et al. | 606/99 |
| 5,322,055 A | 6/1994 | Davison et al. | 601/2 |
| 5,324,297 A | 6/1994 | Hood et al. | 606/99 |
| 5,324,299 A | 6/1994 | Davison et al. | 606/167 |
| 5,397,293 A | 3/1995 | Alliger eta l. | 601/2 |
| 5,413,578 A | 5/1995 | Zahedi | 606/86 |
| 5,417,654 A | 5/1995 | Kelman | 604/22 |
| 5,480,379 A | 1/1996 | La Rosa | 604/22 |
| 5,531,597 A | 7/1996 | Foulkes et al. | 433/119 |
| 5,653,724 A | 8/1997 | Imonti | 606/169 |
| 5,669,922 A | 9/1997 | Hood | 606/169 |
| 5,676,649 A | 10/1997 | Boukhny et al. | 604/22 |
| 6,024,750 A | 2/2000 | Mastri et al. | 606/169 |

BALANCED ULTRASONIC BLADE INCLUDING A PLURALITY OF BALANCE ASYMMETRIES

This is a continuation of application Ser. No. 09/499,989 Filed Feb. 8, 2000 now U.S. Pat. No. 6,328,751; which is a continuation of application Ser. No. 09/106,686 Filed Jun. 29, 1998 now abandaoned.

This application is related to the following co-pending patent applications: application Ser. Nos. 09/106,028; 09/106,415; and 09/106,661 which are hereby incorporated herein by reference.

FIELD OF THE INVENTION

The present invention relates, in general, to curved ultrasonic blades for use in surgical instruments and, more particularly, to balanced curved ultrasonic blades including two or more balance asymmetries.

BACKGROUND OF THE INVENTION

Ultrasonic instruments are often used in surgery to cut and coagulate tissue. Exciting the end effector (e.g. cutting blades) of such instruments at ultrasonic frequencies induces longitudinal vibratory movement which generates localized heat within adjacent tissue, facilitating both cutting and coagulation. Because of the nature of ultrasonic instruments, a particular ultrasonically actuated end effector may be designed to perform numerous functions, including, for example, cutting and coagulation. The structural stress induced in such end effectors by vibrating the blade at ultrasonic frequencies may have a number of undesirable effects. Such undesirable effects may include, for example, substantial transverse motion in the instrument waveguide which may lead to, for example, excess heat generation in the waveguide or premature stress failure. The undesirable effects of vibrating a surgical end effector at ultrasonic frequencies are compounded where the end effector is not symmetrical, that is, where the mass of the end effector is not distributed symmetrically about a line extending through the central axis of the transmission waveguide. Therefore, one way to improve the performance of ultrasonically actuated end effectors is to design end effectors which are substantially symmetric about the central axis of the transmission waveguide. Alternatively, the surgical end effector may be small and short, in which case the end effector will act like a small lumped mass at the end of the transmission waveguide and will not induce substantial transverse motion in the waveguide. Where it is desirable to design end effectors which are not symmetric, performance may be improved by designing the end effector such that the center of mass of the end effector is located along a line which extends through the central axis of the waveguide. One known method of moving the center of mass is to add or subtract mass opposite or close to the asymmetric region until the center of mass lies along a central axis. As a further alternative, longitudinal vibratory motion in the waveguide may be reduced or eliminated by using thicker, more robust waveguides which are not as subject to transverse vibratory motion. However, the use of thick waveguides may not be an acceptable alternative where the ultrasonic surgical instrument is being designed for use in minimally invasive surgery such as endoscopic or laparoscopic surgery. In such instruments it is generally desirable to reduce the diameter of the ultrasonic waveguide in order to fit the instrument through the tiny surgical incisions, narrow body orifices and through trocars presently being used and being designed for future procedures. Long thin ultrasonic waveguides, such as those used in instruments for minimally invasive surgery, are particularly susceptible to transverse vibrations introduced by imbalances in the end effector.

For certain applications, it is desirable to include one or more axially asymmetrical features, (e.g. blade curvature) to enhance performance of the end effector. It may also be desirable to design such end effectors to be relatively long, in order to facilitate certain surgical procedures. In such end effectors, it is not always possible or desirable to include opposed balancing features in the treatment portion in order to balance the end effector by aligning the center of mass with the central axis of the transmission waveguide. It would, therefore, be desirable to design an ultrasonic surgical instrument including a waveguide and an ultrasonic end effector wherein undesirable transverse vibrations resulting from the inclusion of beneficial asymmetrical features (e.g. a long curved blade) in the working portion of the end effector have been reduced or eliminated. It would further be advantageous to design such an instrument wherein the undesirable transverse vibrations have been reduced or eliminated without adding balancing features to the treatment portion of the end effector. It would further be advantageous to design an end effector wherein undesirable transverse vibrations resulting from the inclusion of beneficial asymmetrical features in the treatment portion of the end effector have been reduced or eliminated by adding asymmetrical balancing features proximal to the treatment portion of the end effector. It would further be advantageous to design an asymmetric end effector with a center of mass which is not on the central axis of the transmission wave guide wherein significant transverse motion is not induced in the waveguide by the asymmetric end effector.

SUMMARY OF THE INVENTION

A balanced ultrasonic surgical instrument including an ultrasonic transmission rod and an ultrasonically actuated blade attached to the distal end of the ultrasonic transmission rod. According to the present invention, the ultrasonically actuated blade includes a treatment portion and a balance portion. The treatment portion has a functional feature such as, for example, a curved blade which makes the treatment portion asymmetric. Such a functional feature may be referred to as a functional asymmetry. The balance portion includes at least first and second asymmetric features designed and positioned to balance out any undesirable torque generated by the treatment portion. Such balance features may be referred to as balance asymmetries and may include asymmetric features such as, for example, notches, flats, bumps or raised regions. In an ultrasonic instrument according to the present invention, the balance portion generally extends from a node point on the ultrasonic transmission rod to the proximal end of the treatment portion. In an ultrasonic surgical instrument according to the present invention, the first and second balance asymmetries are positioned such that transverse vibrations in the ultrasonic transmission rod are substantially reduced and may be reduced to approximately zero. Further, in an ultrasonic surgical instrument according to the present invention, the balance ratio of the transmission waveguide may be reduced to less than 1:10 and may be further reduced to less than 1:200.

BRIEF DESCRIPTION OF THE DRAWINGS

The novel features of the invention are set forth with particularity in the appended claims. The invention itself, however, both as to organization and methods of operation, together with further objects and advantages thereof, may best be understood by reference to the following description, taken in conjunction with the accompanying drawings in which:

DETAILED DESCRIPTION OF THE INVENTION

Figure 1:
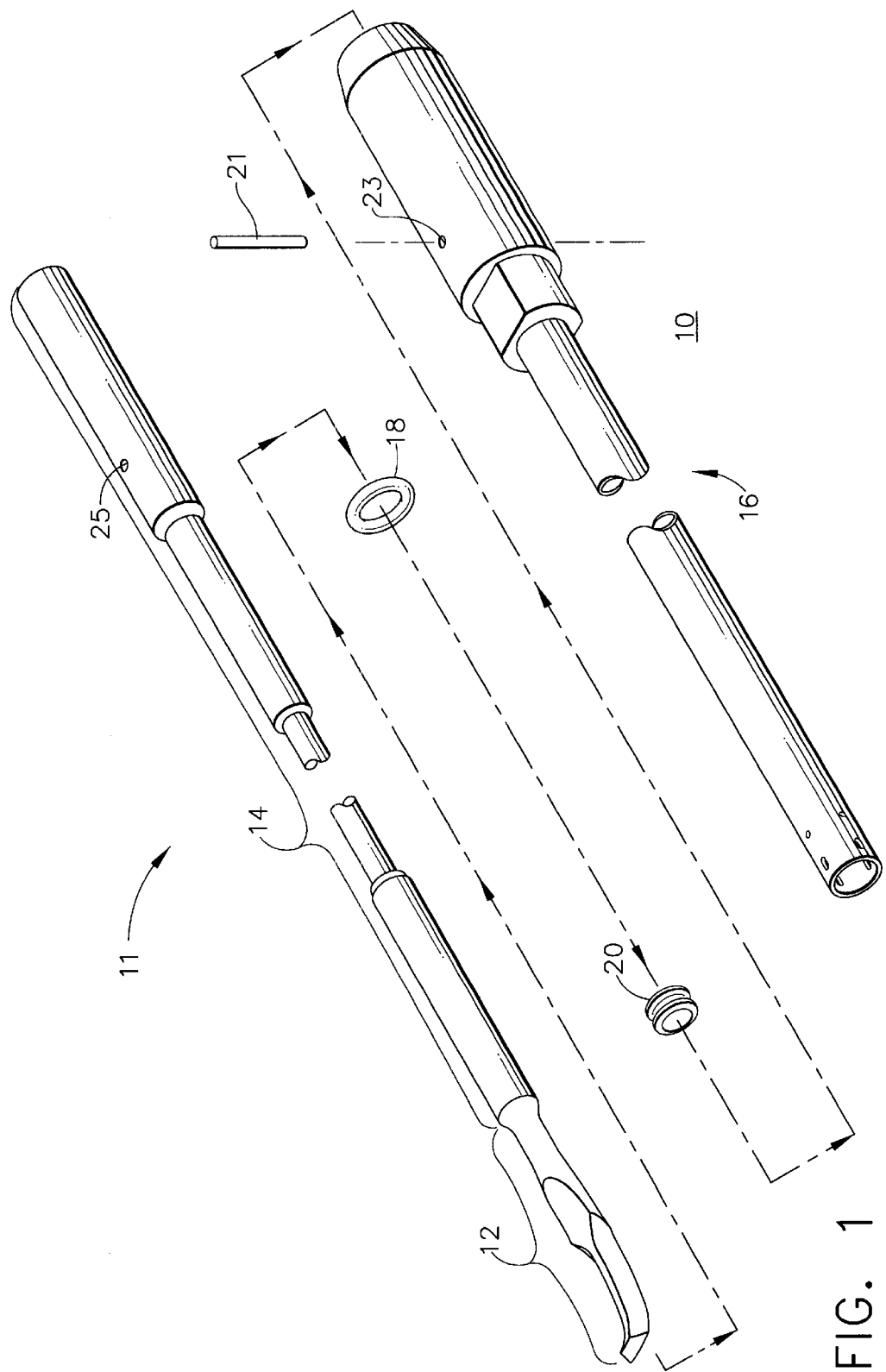
FIG. 1 is an exploded perspective view of an ultrasonic surgical instrument according to the present invention.

FIG. 1 is an exploded perspective view of an ultrasonic surgical instrument 10 according to the present invention. In FIG. 1, ultrasonic end effector 12 is mechanically coupled to ultrasonic transmission waveguide 14 to form ultrasonic transmission assembly 11. Ultrasonic transmission waveguide 14 is positioned in outer sheath 16 by mounting o-ring 18 and sealing ring 20. One or more additional dampers or support members (not shown) may also be included along ultrasonic transmission waveguide 14. Ultrasonic transmission waveguide 14 is affixed to outer sheath 16 by mounting pin 21, which passes through mounting holes 23 in outer sheath 16 and mounting slot 25 in transmission waveguide 14.

Figure 2:
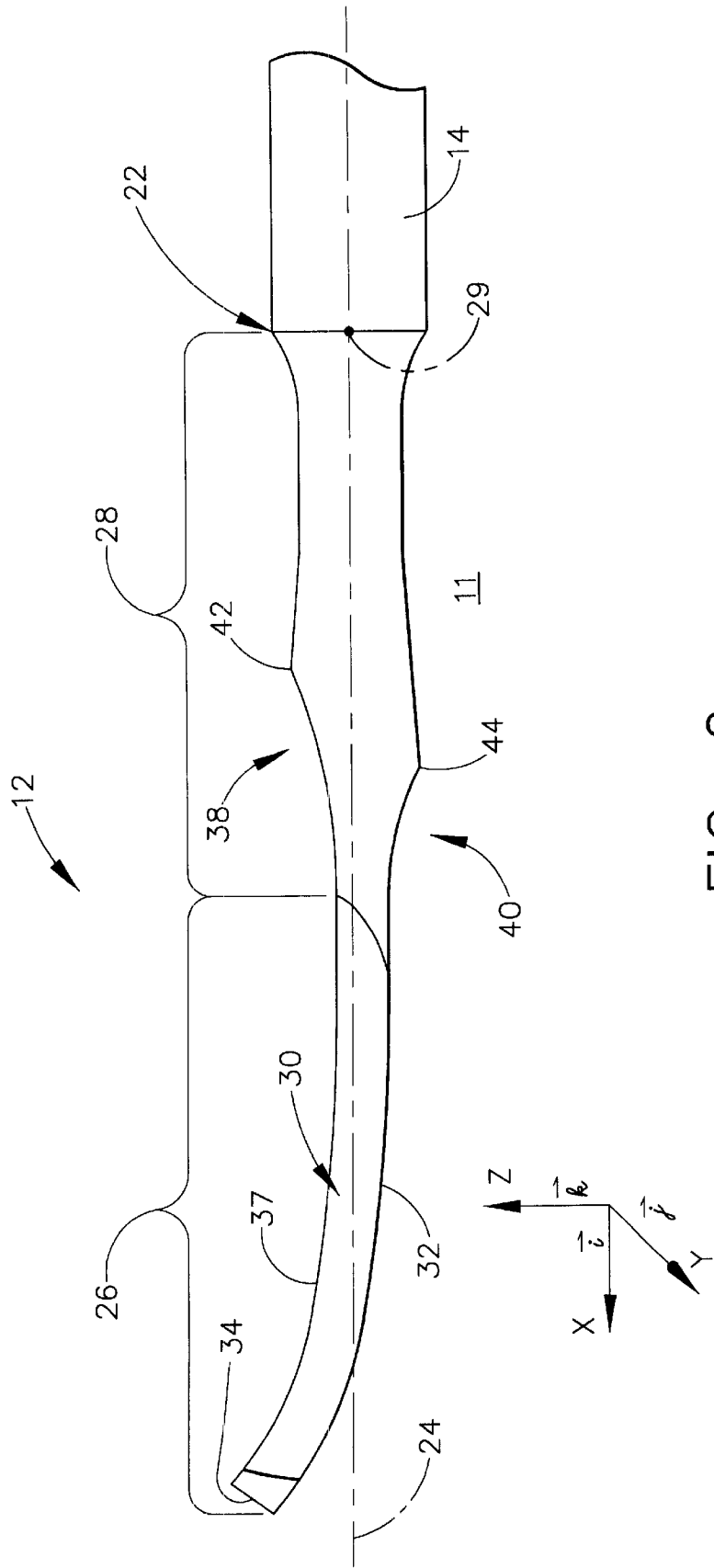
FIG. 2 is a side view of the distal end of an ultrasonic transmission assembly according to the present invention.

FIG. 2 is a side view of the distal end of ultrasonic transmission assembly 11, including end effector 12. FIG. 2 further includes an ordinate system in which: the x-axis lies along central axis 24 of ultrasonic transmission waveguide 14 while the y-axis is the axis of curvature of treatment region 26. In the embodiments of the invention described herein, end effector 12 is affixed to the distal end of transmission waveguide 14 at balance node 22. Central axis 24 of transmission waveguide 14 extends from the proximal end of transmission waveguide 14 to the distal end of transmission waveguide 14. Transmission waveguide 14 is symmetrical about central axis 24. End effector 12 includes treatment region 26, which is located at the distal end of end effector 12 and balance region 28 which is located between treatment region 26 and balance node 22. Treatment region 26, being curved, includes two surfaces, a concave top surface 30 and a convex bottom surface 32. Convex bottom surface 32 is substantially planar or flat along the y-axis of the blade. Treatment region 26 further includes rounded tip 34. In the illustrated embodiment of the invention, balance region 28 includes a first cutout 38 and a second cutout 40 which act as asymmetric balance features. First cutout 38 extending from the proximal end of concave surface 30 to a first predetermined point 42 which is distal to balance node 22. Second cutout 40 extends from the proximal end of convex surface 32 to a second predetermined point 44 which is distal to point 42 and balance node 22.

Figure 3:
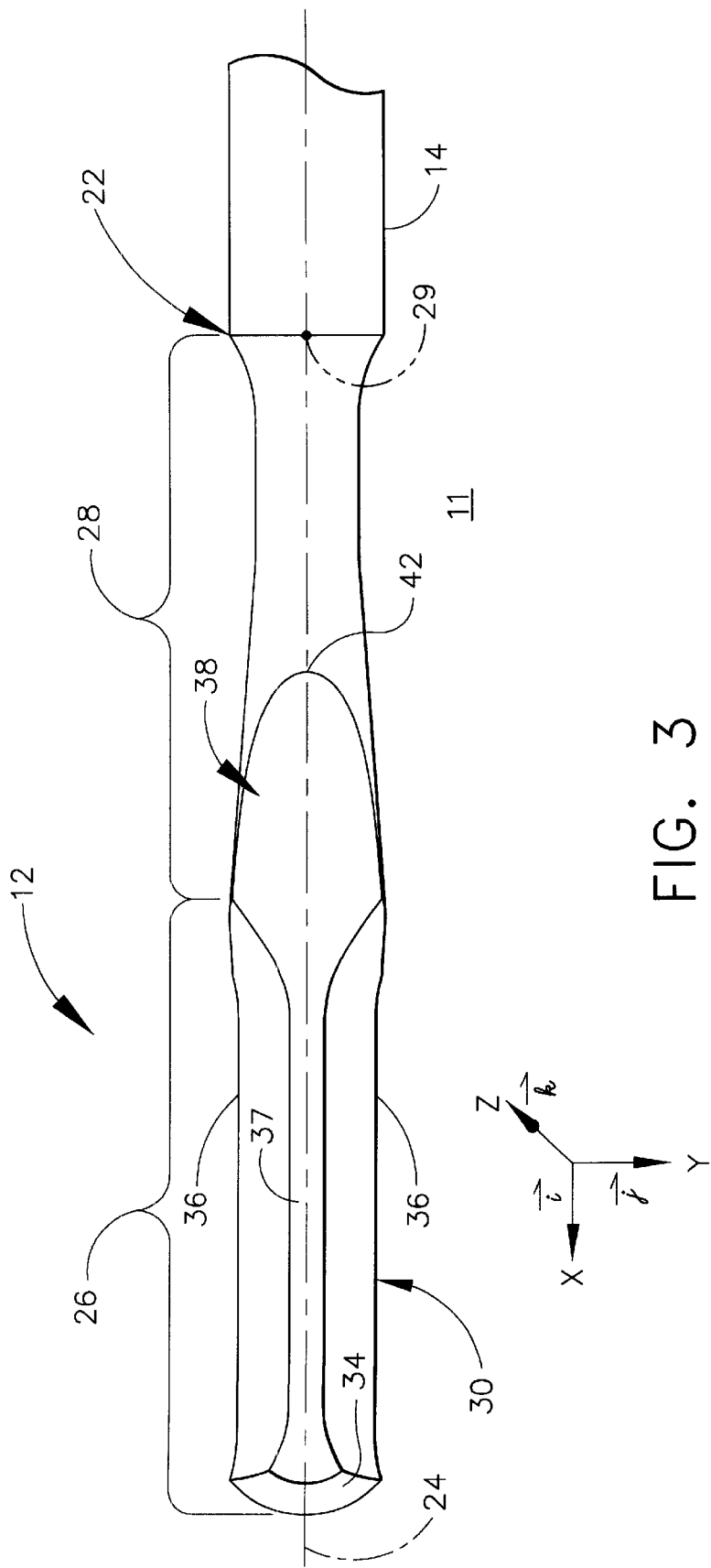
FIG. 3 is a top view of the distal end of an ultrasonic transmission assembly according to the present invention.

FIG. 3 is a top view of the distal end of ultrasonic transmission assembly 11, including end effector 12. In FIG. 3, blade edges 36 are positioned on both sides of treatment region 26 and extend from the proximal end of treatment region 26 to rounded tip 34. The intersection of concave surface 30 and convex surface 32 form blade edges 36. Central ridge 37 runs from the distal end of balance region 28 to rounded tip 34 along the center of treatment region 26. Central ridge 37 forms a portion of concave top surface 30. Central ridge 37 adds strength, stiffness and rigidity to treatment region 26 by giving treatment region 26 a substantially trapezoidal cross-section.

Figure 4:
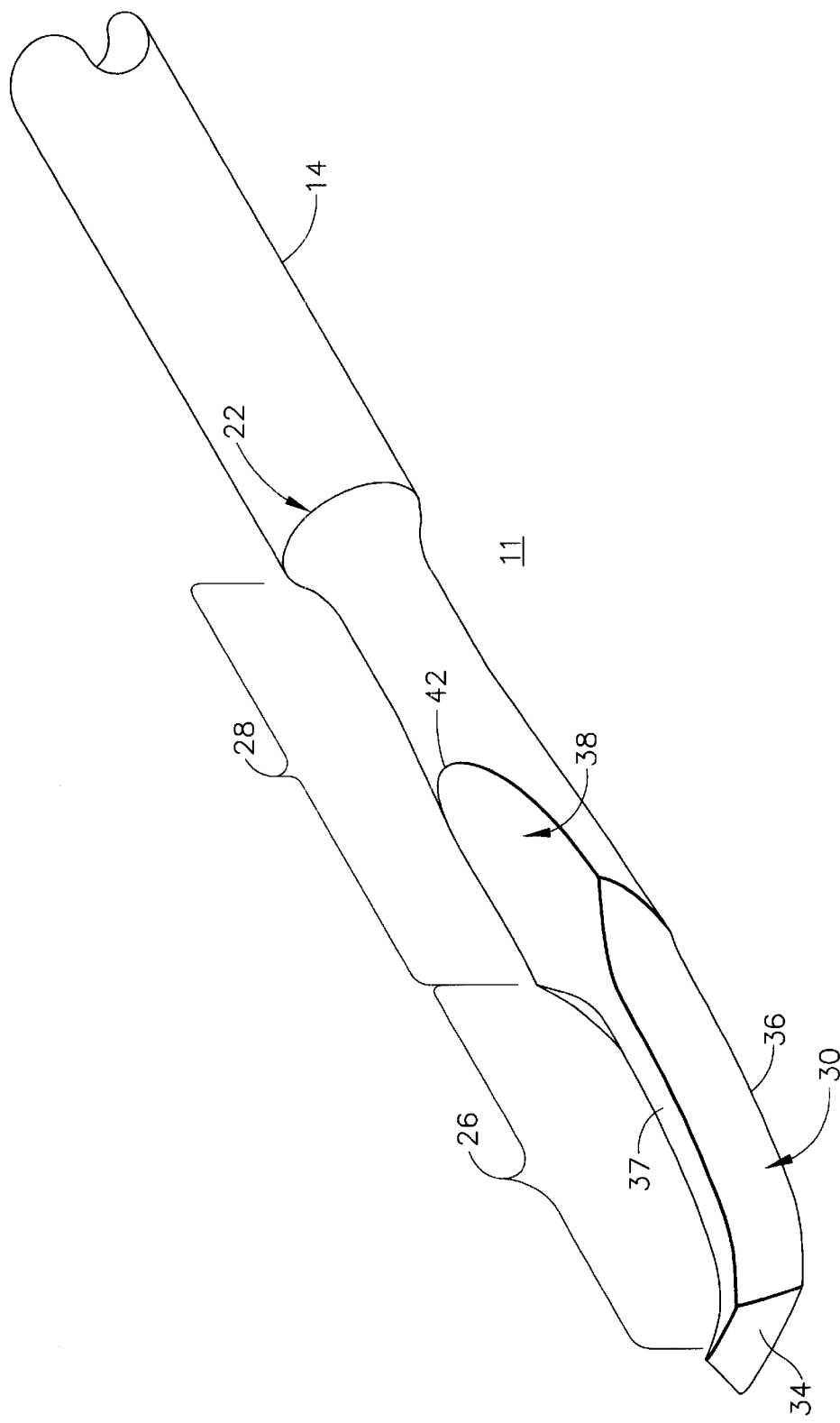
FIG. 4 is a perspective view of the distal end of an alternate embodiment of an ultrasonic transmission assembly according to the present invention.
Figure 5:
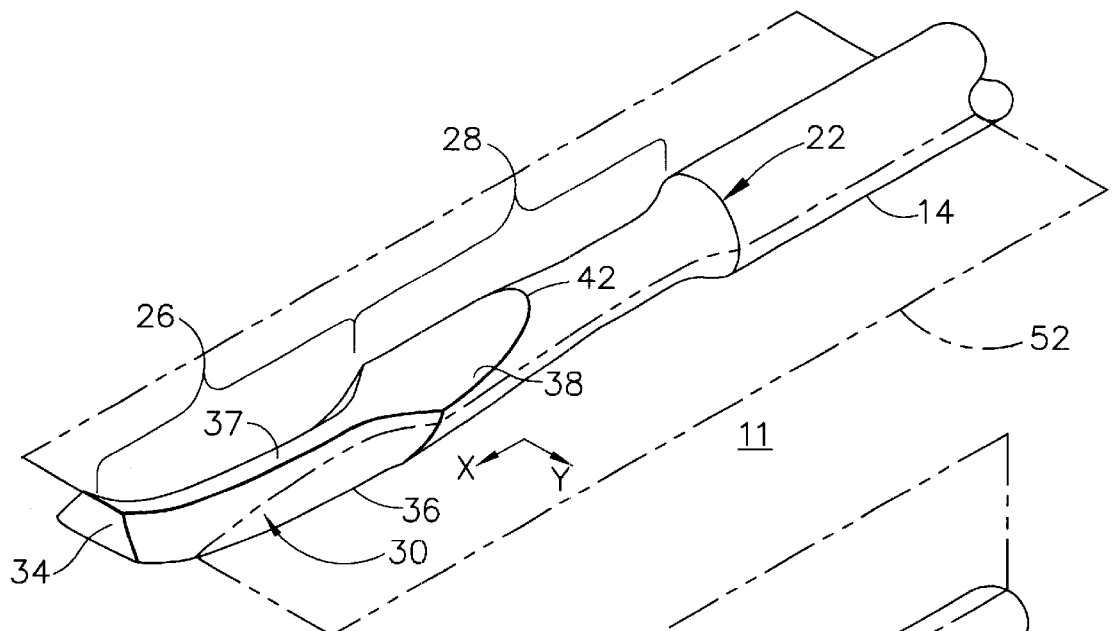
FIG. 5 is a perspective view of the distal end of the ultrasonic transmission assembly shown in FIG. 4 with a phantom x,y plane drawn through the center of the ultrasonic transmission waveguide.

FIG. 4 is a perspective view of the distal end of an embodiment of an ultrasonic transmission assembly 11. FIG. 5 is a perspective view of the distal end of ultrasonic transmission assembly 11 of the embodiment of the invention shown in FIG. 4 with a phantom x,y plane 52 drawn through the center of ultrasonic transmission waveguide 14. In FIG. 5, phantom x,y plane 52 passes through central axis 24. Since treatment region 26 curves away from x,y plane 52, end effector 12 is not symmetrical about x,y plane 52. Plane 52 may, therefore, be referred to as the plane of asymmetry for end effector 12.

Figure 6:
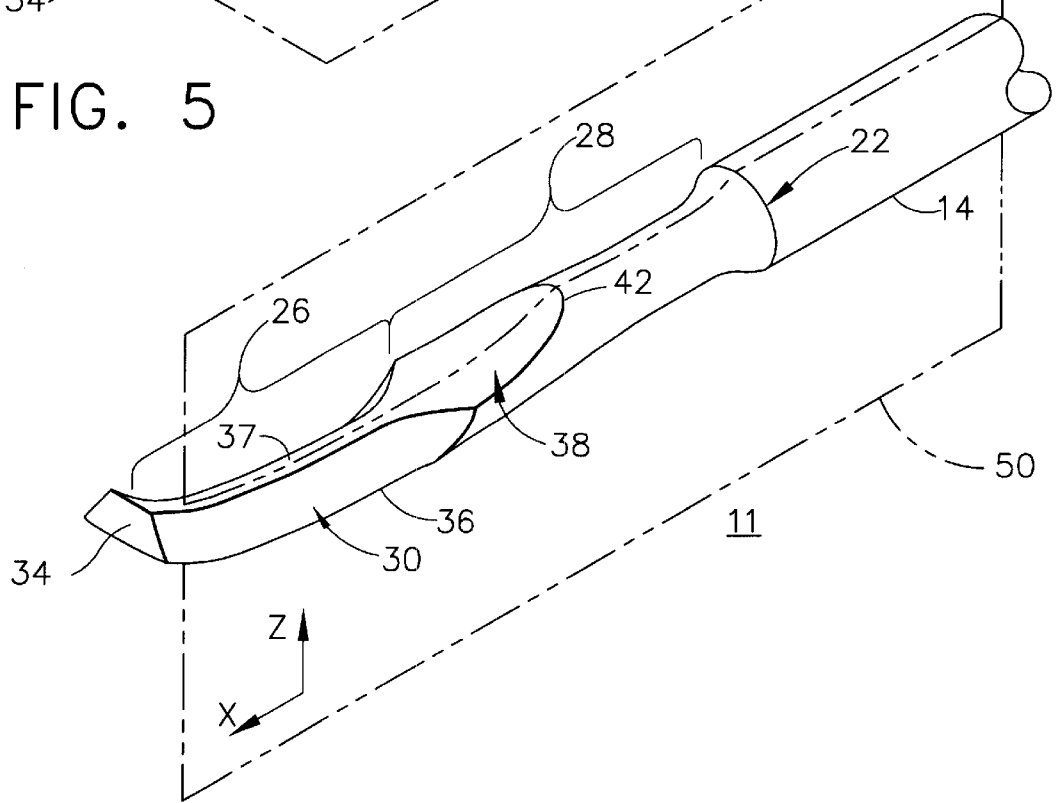
FIG. 6 is a perspective view of the distal end of the ultrasonic transmission assembly shown in FIG. 4 with a phantom x,z plane drawn through the center of the ultrasonic transmission waveguide.
Figure 7:
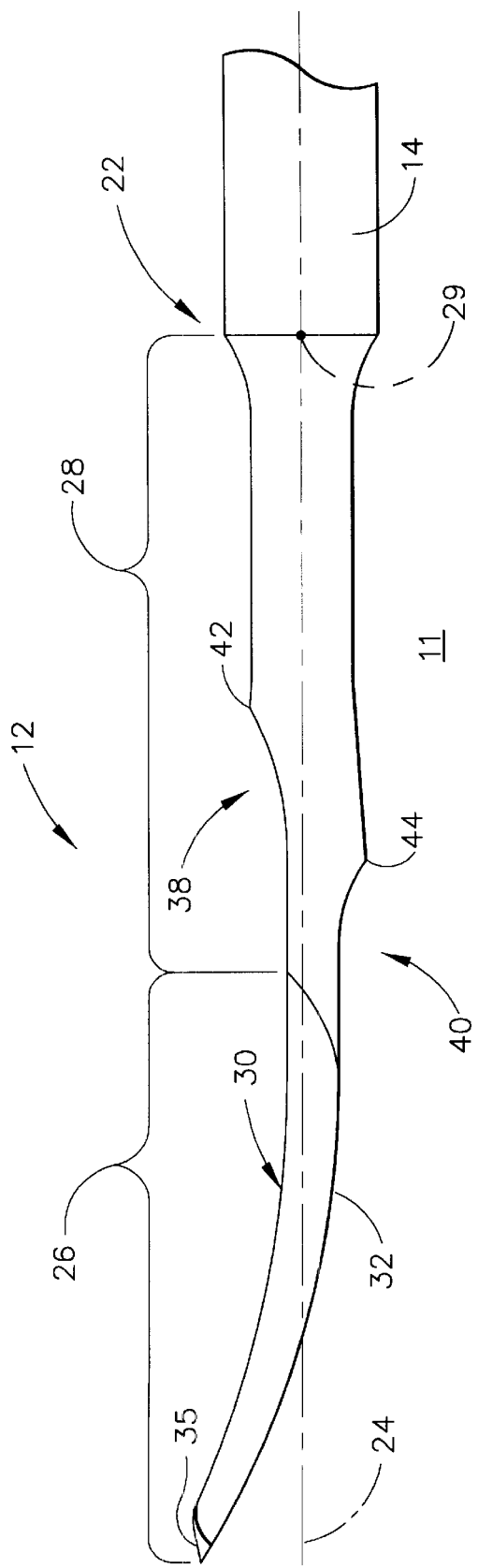
FIG. 7 is a side view of an alternate embodiment of the distal end of the ultrasonic transmission assembly shown in FIG. 4.
Figure 8:
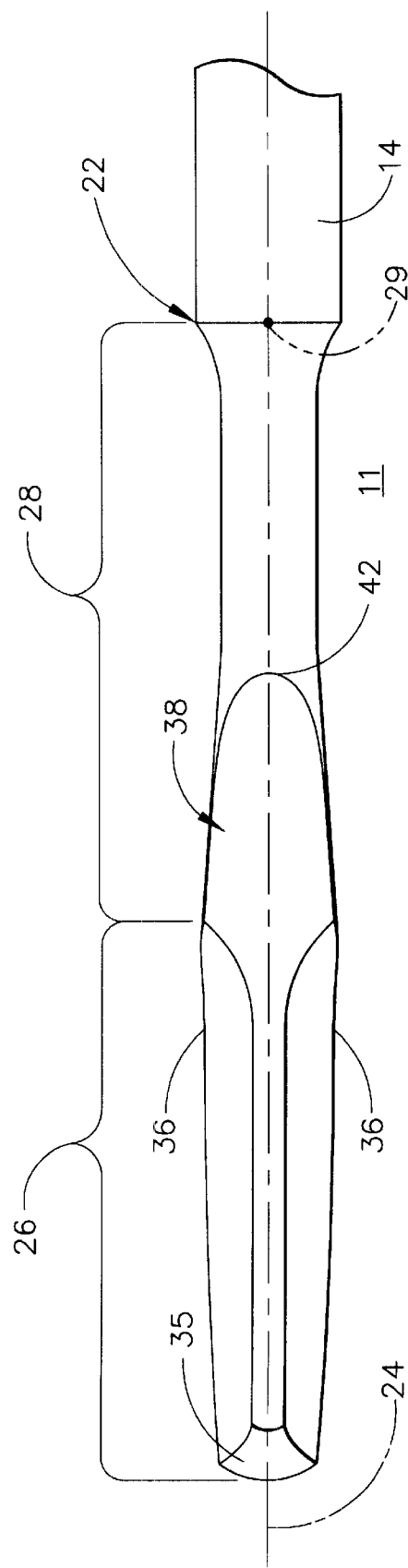
FIG. 8 is a top view of the distal end of the ultrasonic transmission assembly shown in FIG. 7.
Figure 9:
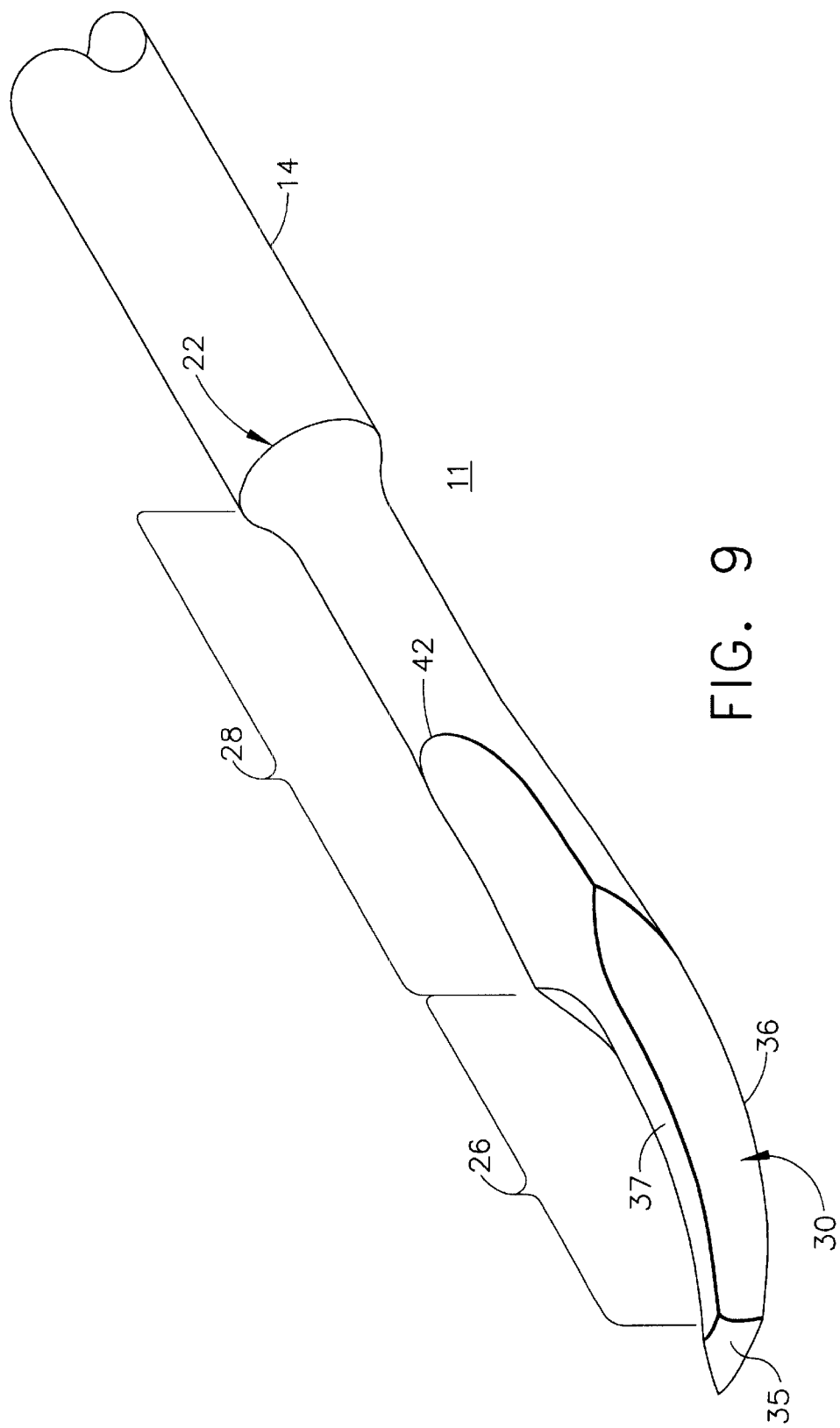
FIG. 9 is a perspective view of the distal end of the ultrasonic transmission assembly shown in FIG. 7.

FIG. 6 is a perspective view of the distal end of the ultrasonic transmission assembly 11 of the embodiment of the invention shown in FIG. 4 with a phantom x,z plane 50 drawn through the center of ultrasonic transmission waveguide 14. In FIG. 6, phantom x,z plane 50 passes through central axis 24 at an angle at 90° to x,y plane 52. End effector 12 is substantially symmetrical about x,z plane 50. Plane 50 may, therefore, be referred to as the plane of symmetry for end effector 12. FIG. 7 is a side view of an alternate embodiment of the distal end of the ultrasonic transmission assembly shown in FIG. 4. In the embodiment of the invention illustrated in FIG. 7, end effector 12 has substantially the same shape and structure as the embodiment of the invention illustrated in FIGS. 1–7 except the embodiment of FIG. 7 includes sharp tip 35 at the distal end of treatment region 26. FIG. 8 is a top view of the distal end of the ultrasonic transmission assembly shown in FIG. 4. FIG. 9 is a perspective view of the distal end of the ultrasonic transmission assembly shown in FIG. 4.

Ultrasonic surgical instrument 10 has a treatment region 26 which includes a curved blade designed to cut and coagulate tissue when vibrated at ultrasonic frequencies, such as, for example, fifty-five kilohertz (55 kHz). Treatment region 26 is curved to provide the surgeon with better access and visibility when using ultrasonic instrument 10. As illustrated in FIGS. 5–6, curved treatment region 26 is symmetrical about x,z plane 50 but is not symmetrical about x,y plane 52. When treatment region 26 is vibrated at an appropriate ultrasonic frequency to facilitate cutting and coagulation, the asymmetrical shape of treatment region 26 will tend to induce undesirable forces, including torque, which are transmitted back to transmission waveguide 14 and induce undesirable transverse vibrations in transmission waveguide 14.

As previously described, it is known that these undesirable transverse vibrations may be minimized and the end effector balanced by designing the end effector such that the center of mass at any point along the end effector is positioned on or very near the central axis of the transmission waveguide. However, where, as in the present invention, the asymmetry (e.g. the curve of treatment region 26), causes the center of mass to diverge substantially from a line extending from the central axis of the transmission waveguide and the addition of balance features within the treatment region is undesirable, the blade must be balanced using an alternative method.

According to the present invention, end effector 12 is balanced by reducing or eliminating the torque induced in end effector 12 proximal to treatment region 26 as a result of including functional asymmetrical features in treatment region 26. A convenient physical point of reference at the proximal end of end effector 12 is balance node 22. It should be noted that balance node 22 may be any node of longitudinal vibration along transmission waveguide 14 and is not necessarily the most distal vibratory node. Nodes of longitudinal vibration occur at half wavelength intervals along the transmission waveguide, wherein the wavelength of interest is the wavelength of the frequency at which the ultrasonic end effector is driven (e.g. 55 kHz). In the embodiment of the invention illustrated in FIG. 3, the asymmetric functional features comprise curved treatment region 26 having rounded tip 34. A feature is asymmetric when its cross-section is not symmetric with respect to waveguide central axis 24. A feature is symmetric when the cross-section is symmetric with respect to waveguide central axis 24. That is, a feature is symmetric when a chord through a cross-section of the portion of the end effector, which includes the feature, is bisected by central axis 24.

According to the present invention, a balance region 28 is included in end effector 12 and end effector 12 is balanced by positioning at least two asymmetric balance features in balance region 28 between the proximal end of treatment region 26 and balance node 22. The size, shape and position of the asymmetric balance features included in balance region 28 are selected to reduce the torque at a balance point 29 to zero or as close to zero as possible. Balance point 29 is on central axis 24 positioned at, for example, balance node 22. The degree to which torque is reduced will depend upon particular design and manufacturing constraints. Thus, by appropriately arranging asymmetric balance features in balance region 28, the torque induced by the asymmetric functional features in treatment region 26 may be canceled by the torque induced by the asymmetric balance features. With the summation of torque distal to end effector 12 minimized, the transverse vibration induced in transmission waveguide 14 will be substantially reduced and may be reduced to approximately zero.

In order to determine whether an asymmetric end effector has been properly balanced, it may be appropriate to measure the torque induced in transmission waveguide 14. The relative magnitude of the torque induced in transmission waveguide 14 may be estimated by taking the ratio of the peak lateral displacement, less Poisson's swelling (also referred to as longitudinal node swelling), at any transverse vibratory antinode of the transmission wave guide to the peak longitudinal displacement at any longitudinal vibratory antinode of the transmission waveguide. The closer the ratio is to zero, the less transverse vibration is being induced in the waveguide. Thus, the ratio of peak lateral displacement to peak longitudinal displacement may be referred to as the "balance ratio". In one embodiment of the present invention, a blade would be considered balanced if the balance ratio of peak lateral displacement to peak longitudinal displacement is 1:10 or less. More particularly, using the techniques described herein, it may be possible to achieve balance ratios of 1:200 or less.

An asymmetric feature is a feature of the end effector wherein the center of mass of the feature is off a line extending from the central axis of the transmission waveguide. In an end effector having a symmetrical orientation and an asymmetrical orientation, such as the end effector illustrated in the Figures, all of the asymmetric features are in a plane parallel to the plane of symmetry.

The mass and shape of the asymmetric balance features introduced into balance region 26 are determined by a number of factors. The torque induced at balance point 29 is equal to the integral over volume of the cross product of the vector acceleration at each point on the end effector with a position vector multiplied by a density scalar. The density scaler is a function which represents the density of the end effector at each point on the end effector. Expressing that equation mathematically, the torque ($\vec{T}$) at balance point 29 is $$\int_{x_0}^{x_1}\int_{y_0}^{y_1}\int_{z_0}^{z_1} \vec{A}(x, y, z) \times \vec{o}(x, y, z) \rho(x, y, z) dz\, dy\, dx, \qquad (1)$$

where:

$x_0$, $y_0$, and $z_0$ are located in the plane x=0 at balance point 29;

$x_1$, $y_1$, and $z_1$ are located in a plane tangential to the distal tip of end effector 12 and, with $x_0$, $y_0$, and $z_0$, define a region which encloses end effector 12;

$\vec{A}(x, y, z)$ is the acceleration of the blade at any point (x,y,z);

$\vec{o}(x, y, z)$ is a vector indicative of the position of the point (x,y,z) with respect to balance point 29; and $\rho(x, y, z)$ is the density of the blade at any point (x,y,z).

Therefore, in a balanced end effector designed according to the present invention, an end effector 12 is first designed which incorporates one or more beneficial asymmetries in treatment region 26 (e.g. curved blade edges 36). A balance node point is then selected at a convenient vibratory node along waveguide 14. Normally the balance node point will be the most distal vibratory node on waveguide 14. A symmetrical (e.g. cylindrical) balance region 28 is then incorporated into end effector 12. In the illustrated embodiments, balance region 28 extends from balance node 22 to the proximal end of treatment region 26. Normally the proximal end of treatment region 26 will correspond with the proximal end of the proximal most beneficial asymmetry. For example, in the embodiment of the invention illustrated in FIG. 2, the proximal end of treatment region 26 corresponds to the proximal end of curved blade edge 36. Once the appropriate beneficial asymmetries have been designed into the end effector, the torque induced at balance point 29 by the end effector design, including beneficial asymmetries, may be calculated using Equation (1) above.

In using Equation (1) above to calculate the torque induced by any particular asymmetry at balance point 29, a suitable first step is to find a mathematical expression for $\vec{A}(x, y, z)$, the acceleration at each point along end effector 12, along with a mathematical expression for $\rho(x, y, z)$, the density at each point along end effector 12, and a mathematical expression for $\vec{o}(x, y, z)$, the position vector for each point along end effector 12 with respect to balance point 29. For convenience, $\vec{o}(x, y, z)$ may be referred to as the offset vector. As Equation (1) indicates, the torque induced at balance point 29 by end effector 12 is the volume integral of the cross product of the acceleration vector with the product of the offset vector and scalar density. In Equation (1), the integral is taken over the volume of the end effector. Generally stated, the torque induced at balance point 29 will be equal to the sum of the torques induced by each asymmetry in end effector 12. Thus an optimum design may be obtained where balance asymmetries are incorporated into balance region 28 such that the torque induced by the balance asymmetries cancel the torque induced by the beneficial asymmetries.

In an ideal situation it would be possible to express $\vec{A}(x, y, z)$, $\vec{o}(x, y, z)$, and $\rho(x, y, z)$ using mathematical formulas which could be conveniently integrated over the volume of end effector 12. However, it is generally very difficult to develop such mathematical formulas for ultrasonic surgical end effector geometry because ultrasonic surgical end effectors do not generally assume continuous geometric shapes such as cones or cylinders. Therefore, once the variables have been calculated or modeled, the integral may be calculated using, for example, a numerical integration program. Of the parameters $\vec{A}(x, y, z)$, $\vec{o}(x, y, z)$, and $\rho(x, y, z)$, the most difficult to calculate is generally the acceleration vector $\vec{A}(x, y, z)$ for each point along end effector 12, particularly for end effectors having complex geometry. Therefore, it is usually necessary to use methods other than direct calculation to obtain an approximation of the acceleration at any point along end effector 12. For example, the displacement at each point may be a suitable approximation of the acceleration with a suitable scaling factor. Displacement may be calculated using, for example, finite element analysis of the blade. Alternatively, velocity at each point may be used to obtain an estimate of acceleration at a given frequency. The velocity at specific points may be calculated by, for example, physically observing external points along the blade surface, (e.g. using a laser vibrometer) and assuming that the interior points are acting in the same manner as the surface points. As another example, the velocity of any point along the blade may be approximated as substantially sinusoidal function of the distance from the balance node point.

The calculation of position vector $\vec{o}(x, y, z)$ is generally tied to the method used to calculate $\vec{A}(x, y, z)$. For example, if $\vec{A}(x, y, z)$ is measured or approximated at specific points along the end effector, then $\vec{o}(x, y, z)$ would be the position vector taken at those specific points.

Since ultrasonic instruments according to the present invention normally utilize end effectors constructed of titanium, aluminum or an alloy of titanium or aluminum the density at any point $\rho(x, y, z)$ is a constant. Therefore, in general $\rho(x, y, z) = P$ where P is the density of the material used in the end effector.

In practice, an end effector is designed which incorporates suitable beneficial asymmetries into treatment region 26. Those beneficial asymmetries induce an undesirable torque $\vec{T}_u$ at balance point 29 which may be calculated using Equation (1). Once the undesirable torque $\vec{T}_u$ for a particular design is known, balance asymmetries may be added in balance region 28 to generate a balance torque $\vec{T}_b$ at balance point 29 which cancels the undesirable torque $\vec{T}_u$ generated by the beneficial asymmetries. Adding balance asymmetries to balance region 28 consists of adding or subtracting mass from particular portions of balance region 28. The size and position of the mass added or subtracted is determined not only by the balance torque $\vec{T}_b$ induced at balance point 29 but also by considerations such as the effect upon the look, feel and ergonomics of the end effector. Therefore, once $\vec{T}_u$ is calculated, the designer may begin to add and subtract mass from balance region 28 to create two or more balance asymmetries which induce a beneficial torque at balance point 29.

It may be possible to simplify the calculations required, for example, using suitable assumptions, it is possible to simplify Equation (1) for the purpose of calculating $\vec{T}_b$. In particular, by assuming that the balance asymmetries can be modeled as a series of point masses and neglecting the effect of rotation:

$$\vec{T}_b = \sum_{n=1}^{k} m_n \vec{A}_{s,n} \times \vec{o}_{CM_{m_n}} \qquad (2)$$

where:

$m_n$ is the mass of the end effector at each point n;

$\vec{T}_b$ is the torque induced at balance point 29 by the balance asymmetries designed into balance region 26;

k is the total number of balance asymmetries;

$\vec{A}_{s,n}$ is the average over a surface, or a representative vector acceleration at the point in balance region 26 where mass n is added; and $\vec{o}_{CM_{m_n}}$ is an offset vector pointing to the Center of Mass of mass n.

By designing the balance asymmetries to be symmetrical about plane of symmetry 50, the torque exerted at node 22 may be modeled as being entirely about the y-axis of the end effector. If all balance asymmetries are located on a plane of symmetry 50, equation (2) becomes:

$$\vec{T}_b = m_1 \vec{A}_{s,1} \times \vec{o}_{CM_{m1}} + m_2 \vec{A}_{s,2} \times \vec{o}_{CM_{m2}} + m_3 \vec{A}_{s,3} \times \vec{o}_{CM_{m3}} + \ldots \qquad (3)$$

or $$\vec{T}_b \cdot \vec{j} = m_1 \vec{A}_{s,1} \times \vec{o}_{CM_{m1}} \cdot \vec{j} + m_2 \vec{A}_{s,2} \times \vec{o}_{CM_{m2}} \cdot \vec{j} + m_3 \vec{A}_{s,3} \times \vec{o}_{CM_{m3}} \cdot \vec{j} + \ldots \qquad (4)$$

or, neglecting signs, $$|\vec{T}_b| = \left| \sum_{n=1}^{k} m_n \vec{A}_{s,n} \times \vec{o}_{CM_{n_1}} \right| \qquad (5)$$

It will be apparent that a significant number of combinations of balance asymmetry sizes and shapes may be used to generate an appropriate torque $\vec{T}_b$ at balance node 29. Further, the size and shape of the particular balance asymmetries chosen will be a function of the material used to create those asymmetries. Therefore, the designer is normally left to select balance asymmetries which not only generate the desired balance torque $\vec{T}_b$, but meet other design criteria as well. Thus, the actual design of appropriate balance asymmetries becomes an iterative exercise, with the blade designer selecting preferred shapes and positions for the balance asymmetries then checking those shapes and positions using one of Equation (1), (2) or (5). The shape and size of the balance asymmetries may be adjusted as required to generate $\vec{T}_b$.

An end effector according to the present invention may also be designed using one or more empirical methods such as, for example, using modal analysis. In the empirical methods, the end effector is designed with appropriate beneficial asymmetries included in treatment region 26 and balance region 28 is modeled as a symmetric connector between the treatment region and transmission waveguide 14. Since treatment region 28 includes beneficial asymmetries (e.g. curved blade edges 36) without corresponding balance asymmetries in balance region 28, this first pass end effector will tend to be unbalanced. Once a first pass end effector is developed, a suitable measurement of the torque generated at a preselected point, such as balance point 29, may be selected. For example, the balance ratio of peak lateral displacement to peak longitudinal displacement as measured in the transmission waveguide. The first pass end effector may then be numerically modeled and vibrated using modal analysis or finite element analysis techniques. With the first pass numerical model driven at a suitable generator frequency (e.g. 55 kHz), it is possible, using, for example, finite element analysis programs to determine the ratio of peak lateral displacement to peak longitudinal displacement at selected points along the transmission waveguide. The end effector may then be balanced (i.e. the ratio of peak lateral displacement to peak longitudinal displacement reduced to less than 1:10) by adding or subtracting mass in the balance region. This is, of course, an iterative process which may be enhanced (i.e. fewer iterations required) by the skill and experience of the designer.

A further empirical design technique involves designing a first pass end effector in the manner set forth above. A physical model of the first pass end effector is then built and tested by driving the input of the transmission waveguide at a suitable generator frequency. The frequency at which the end effector is driven may be referred to as the drive frequency. With the first pass end effector driven at the drive frequency, a suitable measurement of the torque generated at the balance node may be selected, for example, the balance ratio can be measured directly from the transmission waveguide. The end effector may then be balanced (i.e. the balance ratio reduced to less than 1:10) by physically adding or subtracting mass in the balance region. This is, of course, an iterative process which may be enhanced (i.e. fewer iterations required) by the skill and experience of the designer. No matter the design method chosen, whether empirical or analytical, if it is an iterative process, the rougher the first approximation used, the more iterations will be necessary to arrive at balanced blade design.

As described herein, balance node 22 was selected as the proximal origin of balance region 26 in order to provide clarity and to set forth a physically definable point of reference which may be located on any transmission waveguide, using either mathematical computation or physical measurements. As it happens, using node 22 as the proximal origin of balance region 26 is also beneficial in that it is believed to make the mathematics set forth herein cleaner and more understandable. However, it should be recognized that using the present invention, the undesirable torque generated in the waveguide will be substantially canceled by the balance torque generated in the wave guide from a point just proximal to the proximal most balance asymmetry. For example, in the embodiment of the invention illustrated in FIG. 2, the torque will converge toward zero in the portion of the waveguide proximal to first predetermined point 42.

While the embodiments illustrated and described herein have beneficial asymmetries in only one direction, the present technique could be used to balance blades having asymmetries in any two or more directions. It will be further be apparent that, in a surgical end effector designed according to the present invention, the center of mass of the end effector may not be positioned on the central axis of the waveguide. A blade according to the present invention may also be designed to include a single or multiple angle of curvature and to include blunt, square or sharp blade edges. A balanced ultrasonic blade designed according to the present invention may be used to perform many open and endoscopic surgical procedures, including: internal mammary artery (IMA) takedown procedures; removal or dissection of the radial artery; breast reduction and reconstruction; and hemorrhoid removal. Ultrasonic blades, according to the present invention, have multiple functions and may include multiple features to facilitate those functions, for example, flats or blunt regions for configuration, sharp or dull edges and serrated blade edges.

While preferred embodiments of the present invention have been shown and described herein, it will be obvious to those skilled in the art that such embodiments are provided by way of example only. Numerous variations, changes, and substitutions will now occur to those skilled in the art without departing from the invention. Accordingly, it is intended that the invention be limited only by the spirit and scope of the appended claims.

What is claimed is:

1. An end effector for use in an ultrasonic surgical instrument, wherein said end effector comprises:
   an ultrasonic transmission rod having a proximal end and a distal end;
   an ultrasonically actuated blade attached to said distal end of said transmission rod, wherein said ultrasonically actuated blade comprises:
   a distal end;
   a proximal end connected to said transmission rod at a longitudinal vibratory node point;
   a treatment portion including at least one functional asymmetry; and
   a balance portion including first and second balance asymmetries wherein said balance portion extends from said distal end of said ultrasonic transmission rod to a proximal end of said treatment portion and said treatment portion extends from a distal end of said balance portion to said distal end of said blade, wherein said first and second balance asymmetries are positioned to counter torque created at said proximal end of said blade by said functional asymmetry.

2. An end effector according to claim 1, wherein said first and second balance asymmetries are positioned such that transverse vibrations in said ultrasonic transmission rod are substantially equal to zero.

3. An end effector according to claim 1 wherein said transmission rod has a balance ratio of less than 1:10.

4. An end effector according to claim 3 wherein said balance ratio of said transmission rod is less than 1:200.

5. An end effector for use in an ultrasonic surgical instrument, wherein said end effector comprises:
   an ultrasonic transmission rod having a proximal end and a distal end;
   a balanced ultrasonically actuated blade attached to said distal end of said transmission rod, wherein said balanced ultrasonically actuated blade comprises:
   a distal end;

a proximal end;

a curved treatment portion; and a balance portion including first and second balance asymmetries wherein said balance portion extends from said distal end of said ultrasonic transmission rod to a proximal end of said treatment portion and said treatment portion extends from a distal end of said balance portion to said distal end of said blade wherein said balance asymmetries are positioned to counter torque created at said proximal end of said blade by said curved treatment portion.

6. An end effector according to claim 5 wherein said end effector has a top surface and a bottom surface, said top surface being concave in said treatment portion and said bottom surface being convex in said treatment region, said first balance asymmetry being positioned on said top surface and said second balance asymmetry being positioned on said bottom surface.

7. An end effector according to claim 6 wherein said first balance asymmetry comprises a first flat region on said top surface of said balance portion.

8. An end effector according to claim 7 wherein said second balance asymmetry comprises a second flat region on said bottom surface of said balance portion.

9. An end effector according to claim 8 wherein said blade is bisected by a plane of symmetry, said blade being substantially symmetrical on either side of said plane of symmetry, said first balance asymmetry comprising a flat surface on said top surface of said blade wherein said flat surface is substantially perpendicular to said plane of symmetry.

10. An end effector according to claim 9 wherein said second balance asymmetry comprises a second flat surface on said bottom surface of said blade, wherein said flat surface is substantially perpendicular to said plane of symmetry.

11. An end effector according to claim 6 wherein at least one of said first and second balance asymmetries comprises a notch in said balance region.

12. An end effector according to claim 6 wherein at least one of said first and second balance asymmetries comprises a raised region including mass added to said balance region.

13. An ultrasonic surgical instrument including a balanced end effector, wherein said end effector comprises:

a handle including an ultrasonic handpiece;

an ultrasonic transmission rod having a proximal end and a distal end, wherein said proximal end is operatively connected to said handpiece;

an ultrasonically actuated blade attached to said distal end of said transmission rod, wherein said ultrasonically actuated blade comprises:
a distal end;
a proximal end connected to said transmission rod at a longitudinal vibratory node point;
a treatment portion including at least one functional asymmetry; and
a balance portion including first and second balance asymmetries wherein said balance portion extends from said distal end of said ultrasonic transmission rod to a proximal end of said treatment portion and said treatment portion extends from a distal end of said balance portion to said distal end of said blade, wherein said first and second balance asymmetries are positioned to counter torque created at said proximal end of said blade by said functional asymmetry.

14. An ultrasonic surgical instrument according to claim 13, wherein said first and second balance asymmetries are positioned such that transverse vibrations in said ultrasonic transmission rod are substantially equal to zero.

15. An end effector according to claim 13 wherein said transmission rod has a balance ratio of less than 1:10.

16. An end effector according to claim 15 wherein said balance ratio of said transmission rod is less than 1:200.

17. An ultrasonic surgical instrument comprising:

a handle;

an ultrasonic transmission rod having a proximal end and a distal end wherein said proximal end is operatively connected to said handle;

a balanced ultrasonically actuated blade attached to said distal end of said transmission rod, wherein said balanced ultrasonically actuated blade comprises:
a distal end;
a proximal end;
a curved treatment portion; and
a balance portion including first and second balance asymmetries wherein said balance portion extends from said distal end of said transmission rod to a proximal end of said treatment portion and said treatment portion extends from a distal end of said balance portion to said distal end of said blade.

18. An ultrasonic surgical instrument according to claim 17 wherein said blade has a top surface and a bottom surface, said top surface being concave in said treatment portion and said bottom surface being convex in said treatment region, said first balance asymmetry being positioned on said top surface and said second balance asymmetry being positioned on said bottom surface.

19. An ultrasonic surgical instrument according to claim 18 wherein said first balance asymmetry comprises a first flat region on said top surface of said balance portion.

20. An ultrasonic surgical instrument according to claim 19 wherein said second balance asymmetry comprises a second flat region on said bottom surface of said balance portion.

21. An ultrasonic surgical instrument according to claim 18 wherein said blade is bisected by a plane of symmetry, said blade being substantially symmetrical on either side of said plane of symmetry, said first balance asymmetry comprising a flat surface on said top surface of said blade wherein said flat surface is substantially perpendicular to said plane of symmetry.

22. An ultrasonic surgical instrument according to claim 21 wherein said second balance asymmetry comprises a second flat surface on said bottom surface of said blade, wherein said flat surface is substantially perpendicular to said plane of symmetry.

23. An ultrasonic surgical instrument according to claim 18 wherein at least one of said first and second balance asymmetries comprises a notch in said balance region.

24. An ultrasonic surgical instrument according to claim 18 wherein at least one of said first and second balance asymmetries comprises a raised region including mass added to said balance region.

\* \* \* \* \*